US00PP31799P2

(12) United States Plant Patent
Podaras

(10) Patent No.: US PP31,799 P2
(45) Date of Patent: May 26, 2020

(54) ***BUDDLEIA* PLANT NAMED 'PODARASNGA3'**

(50) Latin Name: ***Buddleia* x *hybrida (buddleia davidii* x *B. crispa* x *B. alternifolia* x *B. lindleyana)***
Varietal Denomination: PODARASNGA3

(71) Applicant: Early Morning LLC, Greendale, IN (US)

(72) Inventor: Peter Podaras, Tipp City, OH (US)

(73) Assignee: Early Morning LLC, Greendale, IN (US)

( * ) Notice: Subject to any disclaimer, the term of this patent is extended or adjusted under 35 U.S.C. 154(b) by 0 days.

(21) Appl. No.: 16/501,303

(22) Filed: Mar. 20, 2019

(51) Int. Cl.
*A01H 5/02* (2018.01)
*A01H 6/00* (2018.01)

(52) U.S. Cl.
USPC ..... Plt./242
CPC ..... *A01H 6/00* (2018.05)

(58) Field of Classification Search
USPC ..... Plt./242
CPC ..... A01H 5/02; A01H 5/00
See application file for complete search history.

*Primary Examiner* — Kent L Bell
(74) *Attorney, Agent, or Firm* — Barbara Campbell; Cochran Freund & Young LLC

(57) ABSTRACT

A new *Buddleia* plant particularly distinguished by flower color that has a true periwinkle blue that does not have any lavender tones like other *Buddleia* described as blue, very rounded growth habit, flower panicles are smaller but very numerous with exceptionally large individual flowers that is unique to any cultivar known to the inventor, and individual flowers that are often fully double, is disclosed.

2 Drawing Sheets

Genus and species: *Buddleia* x *hybrida* (*Buddleia davidii* x *B. crispa* x *B. alternifolia* x *B. lindleyana*).
Variety denomination: 'PODARASNGA3'.

BACKGROUND OF THE NEW PLANT

The present invention relates to a new and distinct variety of *Buddleia* hereinafter referred to by the variety name 'PODARASNGA3'.

'PODARASNGA3' arose from a controlled cross in Jul. 15, 2014 in Davis, Calif. between an unnamed and unpatented *Buddleia davidii* x *B. crispa* x *B. alternifolia* x *B. lindleyana* female parent, and an unnamed and unpatented *Buddleia davidii* x *B. crispa* x *B. alternifolia* x *B. lindleyana* male parent. Seeds from the cross were sown in April 2015 and 'PODARASNGA3' was selected in August 2015 from the seedling population.

'PODARASNGA3' was first asexually propagated in August 2016 in Wasco, Calif. by softwood cuttings. 'PODARASNGA3' was found to reproduce true to type in successive generations of asexual propagation via softwood cuttings.

SUMMARY

The following are the most outstanding and distinguishing characteristics of this new variety when grown under normal horticultural practices in Wasco, Calif. and Tipp City, Ohio.

1. Flower color that has a true periwinkle blue that does not have any lavender tones like other *Buddleia* described as blue;
2. Very rounded growth habit;

3. Flower panicles are smaller but very numerous with exceptionally large individual flowers that is unique to any cultivar known to the inventor; and
4. Individual flowers are often fully double.

DESCRIPTION OF THE PHOTOGRAPHS

This new Butterfly bush is illustrated by the accompanying photographs which shows the plant's overall plant habit including form, fruit, and foliage. The photographs are of a 2-year-old plant taken in July 2018 and grown outdoors in Tipp City, Ohio. The colors shown are as true as can be reasonably obtained by conventional photographic procedures.

DESCRIPTION OF THE NEW VARIETY

Figure 1:
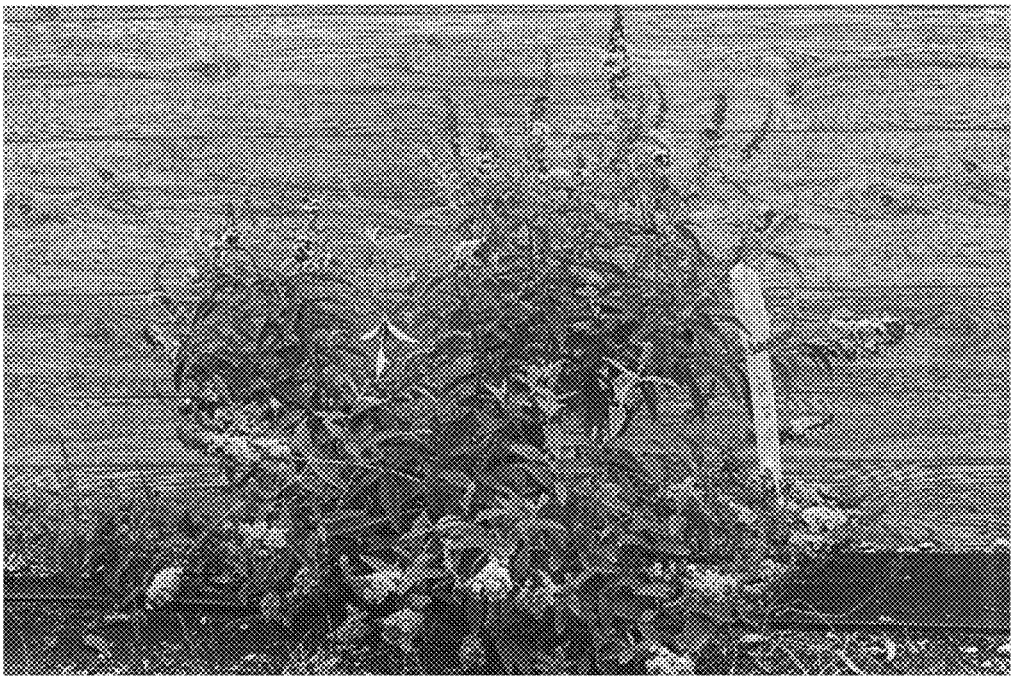
FIG. 1 shows the overall plant habit.
Figure 2:
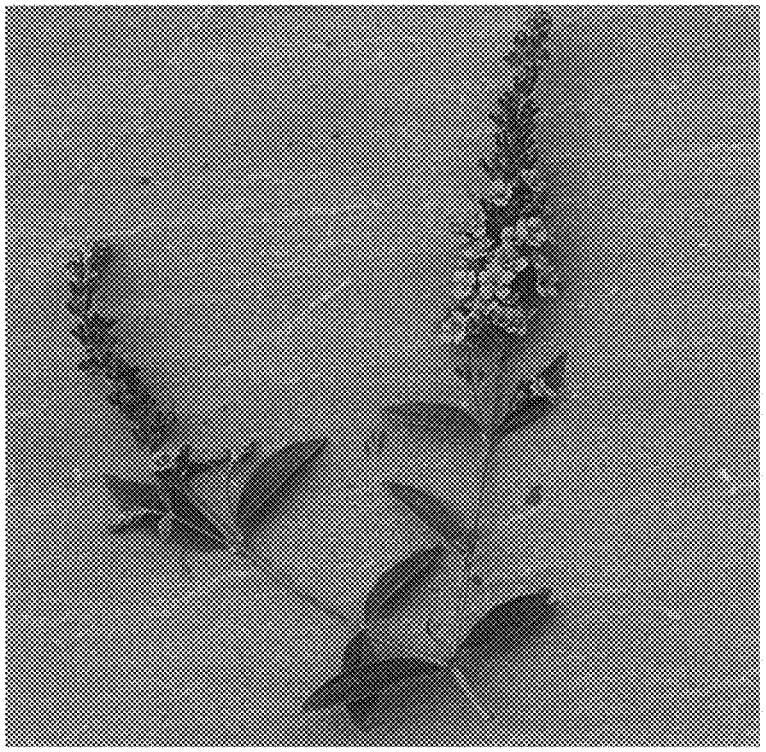
FIG. 2 shows two individual flowering stems from 'PODARASNGA3' at different stages of flowering.
Figure 3:
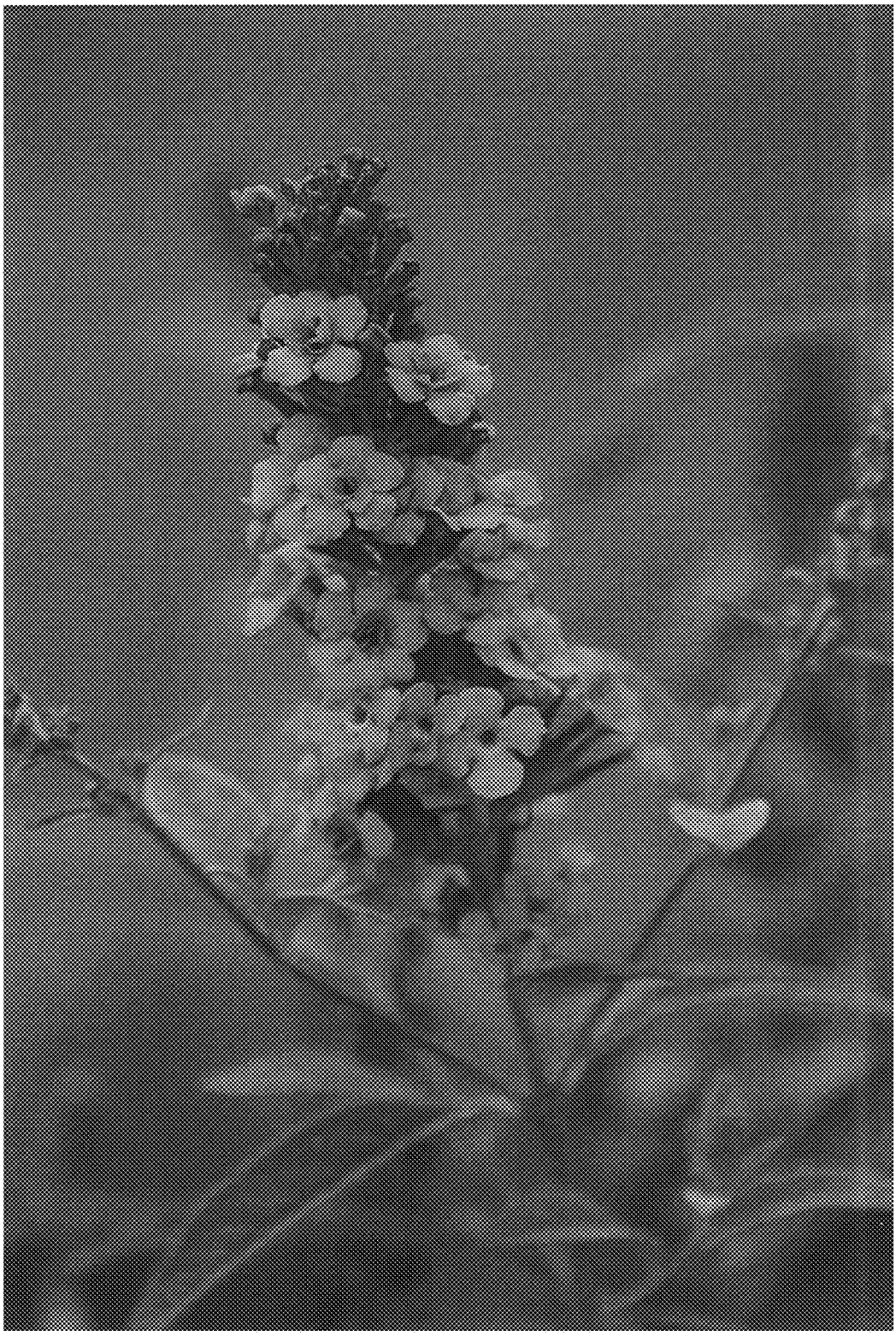
FIG. 3 shows a close-up of an inflorescence with the individual florets at various stages of bloom.

The following detailed descriptions set forth the distinctive characteristics of 'PODARASNGA3'. Measurements were taken from a 2-year-old plant that has been cut back to the ground at the start of its second season of growth and grown outdoors in Tipp City, Ohio. Color references are to The R.H.S. Colour Chart of The Royal Horticultural Society of London (R.H.S.) 2001, Fourth Edition.

Classification:

*Family*.—Scrophulariacace.

*Botanical*.—*Buddleia* x *hybrida* (*Buddleia davidii* x *B. crispa* x *B. alternifolia* x *B. lindleyana*).

*Designation*.—'PODARASNGA3'.

Plant:

*Form*.—Shrub.

*Habit*.—Very rounded.

*Height* (*measured from the top of the soil*).—102 cm to 124 cm.

*Width* (*horizontal plant diameter*).—125 cm.

*Time to produce a finished plant*.—6 to 10 weeks depending on pot size.

*Outdoor plant performance*.—Very good.

*Natural flowering season*.—Late June to frost.

*Time to initiate and develop roots*.—5 to 7 days with 1,500 to 3,000 ppm IBA.

*Root description and habit*.—Dense and fibrous.

*Propagation type*.—Softwood cuttings.

Lateral branches:

*Quantity per plant*.—7.

*Length*.—Up to 44.0 cm.

*Internode length*.—4.0 cm.

*Diameter* (*from midpoint*).—0.38 cm.

*Color*.—RHS 146C.

*Strength*.—Strong and pliable.

*Texture*.—Mostly smooth with minute raised bumps scattered evenly across the surface; occasional stellate hairs.

*Anthocyanin*.—Present, RHS 165A.

Leaves:

*Quantity of leaves per branch*.—24 to 36.

*Arrangement*.—Opposite.

*Shape*.—Lanceolate.

*Apex*.—Acute.

*Base*.—Attenuate, acute.

*Margin*.—Serrate.

*Texture*.—Upper surface: Rugose. Lower surface: Pannose.

*Color, immature*.—Upper surface: RHS 137B. Mature surface: RHS 157A.

*Color, mature*.—Upper surface: RHS 139A. Lower surface: RHS 190D.

*Venation pattern*.—Anastomosing.

*Venation color*.—Upper surface: RHS 139A. Lower surface: RHS 146B.

*Petiole*.—Color: RHS 146B. Length: 0.4 cm. Diameter: 0.2 cm. Texture: Smooth underneath but some appressed stellate hairs on the top.

Inflorescence (panicle):

*Appearance*.—Panicles are roughly conical in shape.

*Height*.—4 cm or up to 20.0 cm.

*Width*.—2.2 cm.

*Bud*.—Shape: Oval. Color: RHS 194C. Height: 1.0 cm. Diameter: 0.45 cm.

*Flower*.—Type and habit: Single and double and salverform flowers arranged in compound terminal panicles; flowers face upright and outward. Fragrance: Very strong and sweet. Lastingness of flowers on the plant: 5 to 10 days. Depth: 1.5 cm. Diameter: 0.3 cm. Quantity per inflorescence: 20 to 130.

*Petals*.—Arrangement: Mostly either 4 or 5 petals per flower, but as many as 12 on occasion, and arranged in a single whorl with the petals fused at the base. Length: 0.4 cm. Width: 0.45 cm. Shape: Almost reniform/obtuse. Apex: Obtuse. Base: Truncated at the corolla tube. Margin: Sinuate to crenate, very irregular. Texture: Upper surface: Slightly bullate, smoother towards the sides; hairs present in the medial area. Lower surface: Bullate. Color, immature: Upper surface: RHS 94A. Lower surface: RHS 94B. Color, mature: Upper surface: RHS 91A. Lower surface: RHS 91B.

*Corolla tube*.—Length: 0.9 cm. Width: 0.2 cm. Color: Inner surface: RHS 26A. Outer surface: RHS N77B. Texture: Inner surface: Pilose, downward pointing hairs. Outer surface: Numerous appressed stellate hairs.

*Calyx*.—Arrangement and quantity per flower: Four sepals arranged in a single whorl and fused towards the base. Shape: Apiculate. Sepals: Length: 0.4 cm. Width: 0.1 cm. Shape: Fused ¼ of the way down. Apex: Acute. Base: Obtuse. Margin: Undulate. Texture: Upper surface: Pannose. Lower surface: Smooth with scattered glandular bodies. Color: Upper surface: RHS 194A. Lower surface: RHS 191A.

*Peduncle*.—Length: Up to 3.0 cm. Diameter: Up to 1.5 cm. Strength: Flexible. Color: RHS 146B. Texture: Stellate hairs uniformly present.

*Pedicel*.—Length: 0.05 cm to 0.15 cm. Diameter: 0.05 cm. Color: RHS 146B. Texture: Pannose.

Reproductive organs:

*Stamens*.—Quantity per flower: 4 to 5. Filament: Length: Completely fused to the corolla tube. Anther: Length: 0.12 cm. Color: RHS 158D. Pollen amount: Abundant. Pollen color: RHS 158D.

*Pistils*.—Quantity per flower: One. Length: 0.2 cm. Stigma: Color: RHS 146C. Style: Length: 0.8 cm. Color: RHS 145C. Ovary: Width: 0.12 cm. Shape: Oval. Color: RHS 146B.

Seeds: None observed.

Disease and insect resistance: None observed.

COMPARISON WITH COMMERCIAL VARIETY

When 'PODARASNGA3' is compared to the commercial variety 'Podaras #8', also known as 'Blue Heaven' (U.S. Plant Pat. No. 22,069), 'PODARASNGA3' has a more rounded growth habit and larger flowers than 'Podaras #8'.

I claim:

1. A new and distinct variety of *Buddleia* plant named 'PODARASNGA3' as illustrated and described herein.

* * * * *